United States Patent [19]

O'Sullivan et al.

[11] Patent Number: 4,596,777
[45] Date of Patent: Jun. 24, 1986

[54] PROCESS FOR PREPARING (3S)-3-[[[2-(PROTECTED OR UNPROTECTED AMINO)-4-THIAZOLYL]ACETYL]AMINO]-2-OXO-1-AZETIDINESULFONIC ACID AND 4-SUBSTITUTED DERIVATIVES THEREOF

[75] Inventors: Joseph O'Sullivan, Belle Mead; Carol A. Aklonis, North Brunswick, both of N.J.

[73] Assignee: E. R. Squibb & Sons, Inc., Princeton, N.J.

[21] Appl. No.: 521,865

[22] Filed: Aug. 10, 1983

[51] Int. Cl.$^4$ ............ C12P 17/16; C12P 17/14; C12P 11/00; C12R 1/19
[52] U.S. Cl. .................... 435/118; 435/120; 435/129; 435/130; 435/131; 435/849
[58] Field of Search ........... 435/118, 120, 129, 130, 435/131, 183, 849

[56] References Cited

U.S. PATENT DOCUMENTS

| | | | |
|---|---|---|---|
| 3,260,653 | 7/1966 | Kaufmann et al. | 195/36 |
| 3,736,230 | 5/1973 | Delin et al. | 195/36 P |
| 3,806,417 | 4/1974 | Beaucamp et al. | 195/63 |
| 3,969,287 | 7/1976 | Jaworek et al. | 260/8 |
| 4,038,140 | 7/1977 | Jaworek et al. | 195/63 |
| 4,182,695 | 1/1980 | Horn et al. | 260/6 |
| 4,443,374 | 4/1984 | Cimarusti et al. | 260/245.4 |

FOREIGN PATENT DOCUMENTS

| | | | |
|---|---|---|---|
| 0698688 | 11/1964 | Canada | 435/849 |
| 0897618 | 5/1962 | United Kingdom | 435/849 |
| 1348359 | 3/1974 | United Kingdom . | |
| 2071650 | 9/1981 | United Kingdom . | |

OTHER PUBLICATIONS

O'Sullivan et al., "Enzymatic Acylation of Monobactams, The Jour. of Antibiotics, vol. 37, pp. 804-806 (1984).

Primary Examiner—Thomas G. Wiseman
Assistant Examiner—Elizabeth C. Weimar
Attorney, Agent, or Firm—Lawrence S. Levinson; Stephen B. Davis

[57] ABSTRACT

A compound having the formula

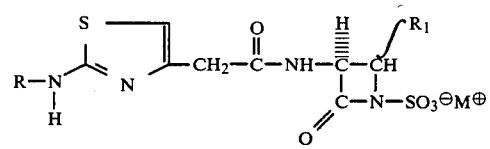

can be prepared by enzymatically coupling a compound of the formula

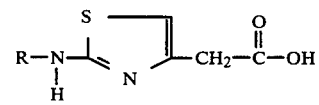

with a compound of the formula

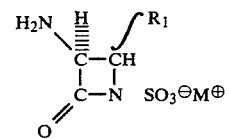

in the presence of *Escherichia coli* acylase at a pH of from about 4.0 to about 6.0.

9 Claims, No Drawings

PROCESS FOR PREPARING (3S)-3-[[[2-(PROTECTED OR UNPROTECTED AMINO)-4-THIAZOLYL]ACETYL]AMINO]-2-OXO-1-AZETIDINESULFONIC ACID AND 4-SUBSTITUTED DERIVATIVES THEREOF

BACKGROUND OF THE INVENTION

United Kingdom patent application No. 2,071,650, published September 23, 1981, discloses β-lactam antibiotics including (3S)-3-[[(2-amino-4-thiazolyl) [(1-carboxy-1-methylethoxy)imino]acetyl]amino]-2-oxo-1-azetidinesulfonic acid and 4-substituted derivatives thereof.

*Escherichia coli* acylase has been reported in numerous patents as being useful in preparing 6-aminopenicillanic acid (6-APA) by cleaving the acyl sidechain from Penicillin G under basic conditions as note, for example, U.S. Pat. No. 3,260,653. The use of an immobilized *Escherichia coli* for this purpose has also been reported as note, for example, U.S. Pat. No. 3,736,230.

Dinelli et al. in British Pat. No. 1,348,359 described employing a bound *Escherichia coli* to produce semisynthetic penicillins and cephalosporins from reaction mixtures containing 6-aminopenicillanic acid (6-APA) or 7-amino-cephalosporanic acid (7-ACA) and a suitable carboxylic acid under acidic conditions.

BRIEF DESCRIPTION OF THE INVENTION

The invention is directed to a process of enzymatically coupling a 2-(protected or unprotected amino)-4-thiazoleacetic acid or a salt thereof to a 3-amino-2-oxo-1-azetidinesulfonic acid or 4-substituted derivative thereof in the presence of an *Escherichia coli* acylase to give a (3S)-3-[[[2-(protected or unprotected amino)-4-thiazolyl]acetyl]amino]-2-oxo-1-azetidinesulfonic acid or 4-substituted derivative thereof. The process of the invention can be represented diagrammatically as follows:

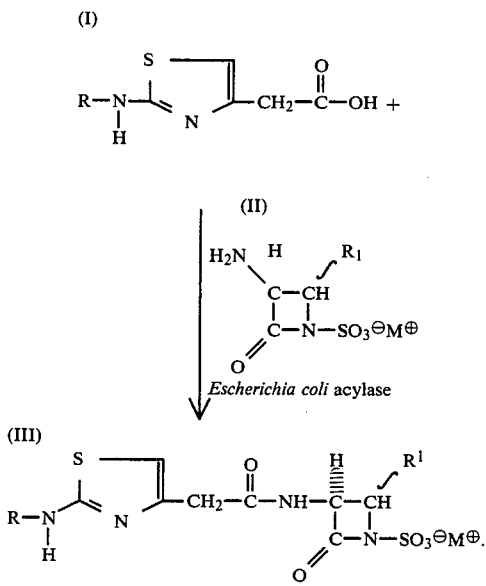

The amides of formula III are useful as intermediates which can be converted to ketoamides of the formula

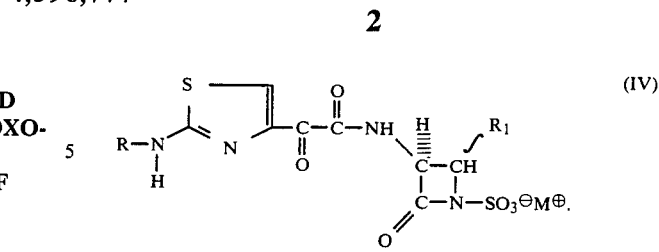

The ketoamides of formula IV are useful as intermediates for the preparation of (3S)-3-[[(2-amino-4-thiazolyl)[(1-carboxy-1-methylethoxy)imino]acetyl]amino]-2-oxo-1-azetidinesulfonic acid and 4-substituted derivatives thereof; i.e., compounds having the formula

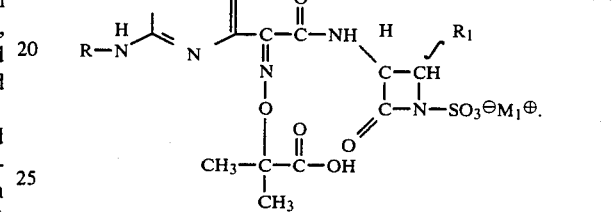

In the above formulas, and throughout the specification, the symbols are as defined below.

R is hydrogen or an amino protecting group;
$R_1$ is hydrogen, methyl, or ethyl;
$M^\oplus$ is hydrogen, an inorganic cation, or a substituted ammonium ion, and
$M_1^\oplus$ is hydrogen, an inorganic cation, or a substituted ammonium ion.

The term "amino protecting group" refers to any group which will protect the nitrogen atom to which it is attached from reacting in the above sequence, and which, at the end of the above-described reaction sequence, can be cleaved from the nitrogen atom under conditions that do not alter the rest of the molecule. Exemplary amino protecting groups are formyl, which is preferred, triphenylmethyl, t-butoxycarbonyl, benzyloxycarbonyl, 1,1-dimethylpropoxycarbonyl, allyloxycarbonyl, and

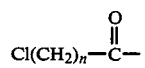

wherein n is 1 to 4, preferably 1 or 4.

The term "inorganic cation" refers to any positively charged inorganic atom or group of atoms. Exemplary inorganic cations are the alkali metals, (e.g., lithium, sodium and potassium), the alkaline earth metals (e.g., calcium and magnesium), manganic, ferrous, cobalt, thallium, manganous, and ammonium ($NH_4^\oplus$).

The term "substituted ammonium ion" refers to organic cations; the tri- and tetra-substituted ammonium ions are specifically contemplated. Exemplary substituted ammonium ions are the pyridinium, triethylammonium, and tetrabutylammonium salts.

DETAILED DESCRIPTION OF THE INVENTION

The process of this invention yields intermediates which can be used to prepare compounds of formula V. Those compounds of formula V wherein R is other than hydrogen can be deprotected to yield the corresponding compound of formula V wherein R is hydrogen. As described in United Kingdom patent application No. 2,071,650, published Sept. 23, 1981, compounds of formula V are β-lactam antibiotics useful for combating bacterial infections (including urinary tract infections and respiratory infections) in mammalian species, such as domesticated animals and humans. It is further disclosed that for combating bacterial infections in mammals, a compound of formula V can be administered to a mammal in need thereof in an amount of about 1.4 mg/kg/day to about 350 mg/kg/day, preferably about 14 mg/kg/day to about 100 mg/kg/day.

The coupling reaction between the aminothiazolylacetic acid of formula I and the azetidinesulfonic acid of formula II is performed by including an *Escherichia coli* acylase within the reaction solution. The *Escherichia coli* acylase may be employed as a solution of the enzyme or in the form of a bound or immobilized enzyme source. In general, any *Escherichia coli* capable of producing an acylase which will cleave Penicillin G, Cephalosporin C, or Cephalosporin G under basic conditions will function under acidic conditions to catalyze this coupling reaction.

A particularly suitable enzyme source is an *Escherichia coli* acylase which is chemically modified and copolymerized in a polyacrylamide matrix according to the procedures described in U.S. Pat. Nos. 3,806,417, 3,969,287, 4,038,140 and 4,182,695. Such an immobilized *Escherichia coli* acylase is commercially available from Boehringer Mannheim.

The enzymatic coupling reaction is carried out under acidic conditions of from about pH 4.0 to 6.0, preferably at about pH 4.5. The coupling reaction is preferably run in an aqueous medium at a temperature of from about 20° C. to about 50° C.

As described in copending U.S. patent application Ser. No. 390,728, filed June 21, 1982 an amide of formula III can be oxidized to yield the corresponding ketoamide of formula IV. A wide variety of oxidation procedures may be used. An exemplary procedure comprises oxidation of an amide of formula III by treatment with potassium nitrosodisulfonate in water, or a mixed aqueous system. Alternatively, oxidation can be accomplished by treatment of an amide of formula III with selenium dioxide in an inert solvent (e.g., dioxane). The oxidation can also be accomplished by the use of metal catalysts in the presence of a suitable co-oxidant. Such combinations include platinum, palladium and other noble metals with air or oxygen as co-oxidants; cupric ion in solution with air or persulfate ion as co-oxidant; ferrous ion in solution with hydrogen peroxide as co-oxidant; and manganic ion, cobalt ion, thallium ion and other transitional metal ions with air or oxygen gas as co-oxidant. The preferred method of oxidation of an amide of formula III comprises treatment with a solution of manganic ion in a suitable solvent, such as acetic acid, in the presence of air or oxygen as co-oxidant.

As described in copending U.S. patent application Ser. No. 344,895, filed Feb. 1, 1982, now U.S. Pat. No. 4,443,374, a ketoamide of formula IV can be condensed in water or in an organic solvent, with 2-aminooxy-2-methylpropanoic acid, or a salt thereof, selectively yielding the corresponding syn-oxime of formula V. If the pH of the condensation reaction mixture is far to the acid side (i.e., about 2.5 or less), the syn-oxime of formula V will be in the form of the zwitterion (i.e., $M_1^{\oplus}$ is hydrogen). If the pH of the condensation reaction mixture is more than about 3.2, the syn-oxime of the formula V will be a salt corresponding to the salt of formula IV (i.e., $M_1^{\oplus}$ in formula V is the same as $M^{\oplus}$ in formula IV).

The [2-(protected amino)-4-thiazolyl]acetic acid compounds of formula I are readily obtained using conventional procedures by protection of the amino group of 2-amino-4-thiazolylacetic acid; see, for example, U.S. patent No. 4,008,246. The (3S)-3-amino-2-oxo-1-azetidinesulfonic acids of formula II are described in the literature; see, for example, United Kingdom patent application No. 2,071,650, published Sept. 23, 1981.

The following examples are specific embodiments of this invention.

EXAMPLE 1

(3S)-3-[[[2-(Formylamino)-4-thiazolyl]acetyl]amino]-4-methyl-2-oxo-1-azetidinesulfonic acid, zwitterion 100 mg. of a *Escherichia coli* acylase that is bound in a polyacrylamide matrix (Boehringer Mannheim) is mixed with an aqueous solution containing 4 mg. of 2-(formylamino)-4-thiazoleacetic acid and an aqueous solution containing 2 mg. of (3S)-3-amino-4-methyl-2-oxo-1-azetidinesulfonic acid, inner salt in a total volume of 2 ml. The pH of the reaction mixture is adjusted to pH 4.5 by the addition of 50 mmolar sodium hydroxide. The reaction mixture is incubated at 30° C. with shaking (60 rpm) for up to 20 hours. The desired product can then be separated from the reaction mixture by thin layer chromatography using a silica gel 60 F254 plate and developing in a solvent consisting of acetonitrile, ethyl acetate, acetic acid, and water (4:4:1:1) followed by elution with water to give (3S)-3-[[[2-(formylamino)-4-thiazolyl]acetyl]amino]-4-methyl-2-oxo-1-azetidinesulfonic acid, zwitterion.

The structure of the product is confirmed by analytical and bioassay techniques.

EXAMPLE 2

(3S)-3-[[[2-(Formylamino)-4-thiazolyl]acetyl]amino]-2-oxo-1-azetidinesulfonic acid, zwitterion Following the procedure of Example 1 but substituting an equivalent amount of (3S)-3-amino-2-oxo-1-azetidinesulfonic acid, inner salt for the 4-methyl reactant, one obtains as a result of the enzymatic coupling (3S)-3-[[[2-(formylamino)-4-thiazolyl]acetyl]amino]-2-oxo-1-azetidinesulfonic acid, zwitterion. Again, the structure is confirmed by analytical and bioassay techniques.

EXAMPLE 3

(3S)-3-[[[2-Amino-4-thiazolyl]acetyl]amino]-4-methyl-2-oxo-1-azetidinesulfonic acid, zwitterion Following the procedure of Example 1 but substituting an equivalent amount of 2-amino-4-thiazoleacetic acid for the formyl protected reactant, one obtains as a result of the enzymatic coupling (3S)-3-[[[2-amino-4-thiazolyl[acetyl]amino]-4-methyl-2-oxo-1-azetidinesulfonic acid, zwitterion. Again, the structure is confirmed by analytical and bioassay techniques.

EXAMPLE 4

(3S)-3-[[[2-Amino-4-thiazolyl]acetyl]amino]-2-oxo-1-azetidinesulfonic acid, zwitterion Following the procedure of Example 1 but substituting an equivalent amount of 2-amino-4-thiazoleacetic acid for the formyl protected reactant and (3S)-3- amino-2-oxo-1-azetidinesulfonic acid, inner salt for the 4-methyl reactant, one obtains as a result of the enzymatic coupling (3S)-3-[[[2-amino-4-thiazolyl]acetyl]amino]-2-oxo-1-azetidinesulfonic acid, zwitterion. Again, the structure is confirmed by analytical and bioassay techniques.

EXAMPLE 5

(3S)-3-[[[2-(Formylamino)-4-thiazolyl]acetyl]amino]-4-ethyl-2-oxo-1-azetidinesulfonic acid, zwitterion Following the procedure of Example 1 but substituting an equivalent amount of (3S)-3-amino-4-ethyl-2-oxo-1-azetidinesulfonic acid, inner salt for the 4-methyl reactant, one obtains as a result of the enzymatic coupling (3S)-[[[2-(formylamino)-4-thiazolyl]acetyl]amino]-4-ethyl-2-oxo-1-azetidinesulfonic acid, zwitterion.

In a similar manner, the reactions described in Examples 1 to 4 can be duplicated by substituting for the polyacrylamide bound acylase an acylase solution obtained from *Escherichia coli* ATCC 13,529.

What is claimed is:

1. A process for preparing (3S)-3-[[[2-(protected or unprotected amino)-4-thiazolyl]acetyl]amino]-2-oxo-1-azetidinesulfonic acid or 4-substituted derivative thereof having the formula

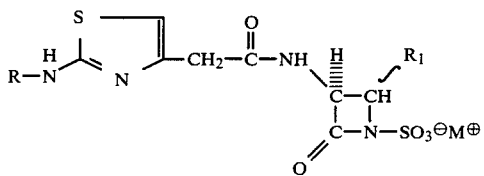

which comprises enzymatically coupling a compound having the formula

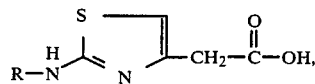

or a salt thereof, with a compound having the formula

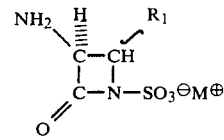

in the presence of an *Escherichia coli* acylase at a pH of from about 4.0 to about 6.0 and recovering said (3S)-3-[[[2-(protected or unprotected amino)-4-thiazolyl]acetyl]amino]-2-oxo-1-azetidinesulfonic acid or 4-substituted derivative thereof from the reaction mixture; wherein R is hydrogen or an amino protecting group;
$R_1$ is hydrogen, methyl or ethyl; and
$M^\oplus$ is hydrogen, an inorganic cation or a substituted ammonium ion.

2. A process of claim 1 wherein:
R is formyl;
$R_1$ is methyl; and
$M^\oplus$ is hydrogen.

3. A process of claim 1 wherein:
R is formyl;
$R_1$ is hydrogen; and
$M^\oplus$ is hydrogen.

4. A process of claim 1 wherein:
R is hydrogen;
$R_1$ is methyl; and
$M^\oplus$ is hydrogen.

5. A process of claim 1 wherein:
R is hydrogen;
$R_1$ is hydrogen; and
$M^\oplus$ is hydrogen.

6. A process of claim 1 wherein the acylase is an *Escherichia coil* acylase that is bound in a polyacrylamide matrix.

7. A process of claim 1 wherein the acylase is obtained from *Escherichia coli* ATCC 13,529.

8. A process of claim 1 wherein said enzymatic coupling therefor reaction is performed in water and the reaction mixture is incubated at about 30° C. for more than about 20 hours.

9. A process of claim 1 wherein said enzymatic coupling reaction is performed at a pH of about 4.5.

* * * * *